(12) United States Patent
Griebling et al.

(10) Patent No.: US 12,697,232 B2
(45) Date of Patent: *Aug. 4, 2026

(54) BIOMEDICAL FINGER ASSEMBLY WITH RATCHETING LOCK

(71) Applicant: RCM Enterprise L.L.C., Olympia, WA (US)

(72) Inventors: Erich Theodore Griebling, Olympia, WA (US); Catherine Rocille Treadwell, Olympia, WA (US); Bradley Arthur Crittenden, Olympia, WA (US)

(73) Assignee: RCM Enterprise L.L.C., Olympia, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/078,693

(22) Filed: Dec. 9, 2022

(65) Prior Publication Data

US 2023/0320873 A1      Oct. 12, 2023

Related U.S. Application Data

(63) Continuation of application No. 17/028,792, filed on Sep. 22, 2020, now Pat. No. 11,554,029.

(Continued)

(51) Int. Cl.
| | |
|---|---|
| *A61F 2/58* | (2006.01) |
| *A61F 2/50* | (2006.01) |
| *A61F 2/68* | (2006.01) |

(52) U.S. Cl.
CPC ...... *A61F 2/586* (2013.01); *A61F 2002/5001* (2013.01); *A61F 2002/5043* (2013.01);
(Continued)

(58) Field of Classification Search
CPC .......................... A61F 2/586; A61F 2002/587
See application file for complete search history.

(56) References Cited

U.S. PATENT DOCUMENTS

| | | | |
|---|---|---|---|
| 1,277,747 | A | 9/1918 | Oconnor |
| 1,484,913 | A | 2/1924 | Meredith |

(Continued)

FOREIGN PATENT DOCUMENTS

| | | |
|---|---|---|
| CN | 204274728 U | 4/2015 |
| CN | 106038009 B | 2/2018 |

(Continued)

OTHER PUBLICATIONS

ISA, International Search Report, PCT Application No. PCT/2020/052066, mailed Dec. 10, 2020, 9 pages.

(Continued)

*Primary Examiner* — David H Willse
(74) *Attorney, Agent, or Firm* — Ashurst Perkins Coie US LLP

(57) ABSTRACT

This disclosure provides systems, apparatuses, and devices for a prosthetic digit usable with persons with amputations at or proximal to the metacarpophalangeal joint. The device restores prehension in a person with missing fingers or thumb by providing opposition to forces in the extension direction via a spring-loaded pawl and locking rack ratchet mechanism, thereby allowing an individual to manipulate or stabilize objects. The digit may be spring-loaded in the extension direction by a torsion spring or other biasing member. The pawl may be automatically disengaged from the rack when the digit reaches full flexion, and the full flexion disengage stop may be adjustable. The pawl may be automatically engaged with the rack when the digit reaches full extension, and the extension stop may be adjustable. The pawl may contain a lateral feature that creates interference with the anchoring linkage under load and limits deflection of the structure.

14 Claims, 12 Drawing Sheets

Related U.S. Application Data

(60) Provisional application No. 62/904,506, filed on Sep. 23, 2019.

(52) U.S. Cl.
CPC .................. *A61F 2002/5073* (2013.01); *A61F 2002/6854* (2013.01)

(56) References Cited

U.S. PATENT DOCUMENTS

| | | | |
|---|---|---|---|
| 2,425,154 A | 8/1947 | Hibbard | |
| 2,493,776 A | 1/1950 | Alberto et al. | |
| 4,074,367 A | 2/1978 | John et al. | |
| 4,685,926 A | 8/1987 | Haupt | |
| 4,685,929 A | 8/1987 | Monestier | |
| 5,800,571 A | 9/1998 | Carlson et al. | |
| 5,941,914 A | 8/1999 | Jacobsen et al. | |
| 9,592,134 B2 | 3/2017 | Varley | |
| 9,913,737 B2 | 3/2018 | Hunter | |
| 9,999,522 B2 | 6/2018 | Gill | |
| 10,653,539 B2 | 5/2020 | Cazenave | |
| 10,869,773 B2 | 12/2020 | Martinez-luna et al. | |
| 10,905,570 B2 | 2/2021 | Segil et al. | |
| 11,083,600 B2 | 8/2021 | Gill | |
| 11,229,533 B2 | 1/2022 | Segil et al. | |
| 11,554,029 B2 * | 1/2023 | Griebling ................ A61F 2/586 |
| 2005/0021154 A1 | 1/2005 | Brimalm | |
| 2006/0212129 A1 | 9/2006 | Lake et al. | |
| 2009/0096746 A1 | 4/2009 | Kruse et al. | |
| 2012/0109337 A1 | 5/2012 | Schulz | |
| 2012/0303136 A1 | 11/2012 | Macduff | |
| 2012/0308806 A1 | 12/2012 | Leto et al. | |
| 2013/0041476 A1 | 2/2013 | Schulz | |
| 2013/0127791 A1 | 5/2013 | Siuta | |
| 2014/0107805 A1 | 4/2014 | Varley | |
| 2014/0114439 A1 | 4/2014 | Iversen et al. | |
| 2014/0303750 A1 | 10/2014 | Macduff | |
| 2015/0190245 A1 | 7/2015 | Mcleary et al. | |
| 2015/0230941 A1 | 8/2015 | Jury | |
| 2016/0015100 A1 | 1/2016 | Leto | |
| 2016/0224138 A1 | 8/2016 | Adkins | |
| 2016/0367383 A1 | 12/2016 | Sensinger et al. | |
| 2017/0007424 A1 | 1/2017 | Gill | |
| 2017/0020691 A1 | 1/2017 | Thompson et al. | |
| 2017/0056208 A1 | 3/2017 | Thompson et al. | |
| 2018/0036145 A1 | 2/2018 | Jury et al. | |
| 2018/0064563 A1 | 3/2018 | Gill | |
| 2018/0110631 A1 | 4/2018 | Cazenave | |
| 2018/0235293 A1 | 8/2018 | Lee et al. | |
| 2018/0296369 A1 | 10/2018 | Smit et al. | |
| 2019/0328550 A1 | 10/2019 | Akhtar et al. | |
| 2019/0374353 A1 | 12/2019 | Schulz | |
| 2020/0054464 A1 | 2/2020 | Sensinger et al. | |
| 2020/0060361 A1 | 2/2020 | Depriest et al. | |
| 2021/0085490 A1 | 3/2021 | Griebling et al. | |
| 2021/0293643 A1 | 9/2021 | Correll et al. | |
| 2021/0361445 A1 | 11/2021 | Griebling et al. | |
| 2022/0133509 A1 | 5/2022 | Segil et al. | |
| 2022/0313456 A1 | 10/2022 | Acevedo et al. | |
| 2024/0390164 A1 | 11/2024 | Griebling et al. | |

FOREIGN PATENT DOCUMENTS

| | | | |
|---|---|---|---|
| CN | 109381285 A | 2/2019 | |
| CN | 110353865 A | 10/2019 | |
| DE | 2329929 A1 | 1/1975 | |
| DE | 102017005761 B4 | 2/2020 | |
| EP | 3110372 B1 | 1/2018 | |
| EP | 3842015 A2 | 6/2021 | |
| EP | 3856088 B1 | 8/2022 | |
| FR | 2277569 A2 | 2/1976 | |
| GB | 145267 * | 7/1920 | ............. A61F 2/586 |
| JP | 2004-041279 A | 2/2004 | |
| JP | 2015146998 A | 8/2015 | |
| WO | 2010018358 A2 | 2/2010 | |
| WO | 2016187133 A1 | 11/2016 | |
| WO | 2017061879 A1 | 4/2017 | |
| WO | 2021061681 A1 | 4/2021 | |
| WO | 2021236370 A1 | 11/2021 | |
| WO | 2022211824 A1 | 10/2022 | |
| WO | 2023080796 A1 | 5/2023 | |

OTHER PUBLICATIONS

European Application No. 20869041.2 Extended Supplementary Search Report and Opinion Mailed Sep. 8, 2023, pp. 1-6.

ISR from PCT Application No. PCT/2020/052066, mailed Dec. 10, 2020, 9 pages.

Japanese Application No. 2022-517781 Office Action Mailed May 20, 2024, pp. 1-6.

Segil, Jacob L. et al. "The Point Digit: Mechanical Design and Testing of a Ratcheting Prosthetic Finger," Abstract, 41st Annual Meeting of the American Society of Biomechanics, Boulder CO, Aug. 8-11, 2017, 2 pages.

U.S. Appl. No. 17/316,357 Non-Final Office Action Mailed May 17, 2023, pp. 1-19.

U.S. Appl. No. 17/316,357, Non-Final Office Action Mailed Jan. 23, 2024, pp. 1-19.

U.S. Appl. No. 17/346,126, Non-Final Office Action Mailed Jan. 9, 2024, pp. 1-25.

Ventimiglia, Paul. Major Qualifying Project submitted to Faculty of Worchester Polytechnic Institute, "Design of a Human Hand Prosthesis," Apr. 26, 2012, 75 pages.

ISR from International Application No. PCT/US2021/031637 dated Sep. 10, 2021.

Extended European Search Report from European Application No. 21935405, dated Jan. 15, 2025.

ISR from International Application No. PCT/US2021/026909, dated Jul. 21, 2021.

U.S. Appl. No. 17/346,126 Final Office Action mailed Aug. 5, 2024.

U.S. Appl. No. 17/316,357 Final Office Action Mailed Jul. 24, 2024.

Extended European Search Report from European Application No. 21809498.5, dated May 31, 2024.

ISR from PCT Application No. PCT/US2024/031109, dated Aug. 23, 2024.

U.S. Appl. No. 17/316,357, Non-Final Office Action Mailed Jun. 23, 2022.

U.S. Appl. No. 17/221,722, Notice of Allowance Mailed Dec. 4, 2024.

U.S. Appl. No. 17/221,722, Non-Final Office Action Mailed Jan. 19, 2024.

U.S. Appl. No. 17/221,722, Final Office Action Mailed Oct. 20, 2023.

U.S. Appl. No. 17/221,722, Non-Final Office Action Mailed Apr. 12, 2023.

Examination Report from EP Application No. 21809498.5, dated Jan. 31, 2025.

Examination Report From Australian Application No. 2020354470, dated Mar. 7, 2025.

Office Action and Search Report received for Chinese Application No. 202180059034, mailed on Jan. 4, 2026, 25 pages (12 pages of original office action and 13 pages of English Translation).

* cited by examiner

BIOMEDICAL FINGER ASSEMBLY WITH RATCHETING LOCK

CROSS REFERENCE TO RELATED APPLICATION

This application is a continuation of U.S. patent application Ser. No. 17/028,792, filed Sep. 22, 2020, now issued as U.S. Pat. No. 11,554,029, and claims priority to U.S. Provisional Patent Application No. 62/904,506, filed Sep. 23, 2019, both of which are hereby incorporated by reference in their entirety.

TECHNICAL FIELD

The present technology generally relates to an adjustable prosthesis to replace finger(s) or a thumb at or proximal to the metacarpophalangeal joint.

BACKGROUND

Partial hand loss is the most common upper extremity amputation and has historically been underserved by conventional treatment. Most partial hand amputations are traumatic in origin, and many amputations occur in workplaces where manual labor is performed. Partial hand loss alters the ability to sort mail, play an instrument, return to a vocation, or even dress oneself and cut or hold food. The injury is so devastating that manual laborers are often unable to return to the same line of work.

The primary goal of functional partial hand prosthetic intervention is to restore opposition grasp: a sufficiently forceful grasp between the thumb and the fingers such that objects can be stabilized and manipulated. Conventional technology, however, has struggled to provide restorative interventions because of the wide range of anatomical and functional presentations post-amputation, and the complexity of replacing a powerful, dexterous, and small portion of the human hand. Partial hand loss includes any amputation distal to or through the carpal bones, including finger loss. Within this definition, four distinct zones can be considered: (1) distal to the metacarpophalangeal joint (MCP, or "knuckle"); (2) at or proximal to the MCP joint, but distal to the carpal bones (transmetacarpal); (3) at the carpal bones; and (4) thenar (full or partial thumb).

Available prosthetic interventions for transmetacarpal partial hand amputees can be broadly divided into three categories: (1) cosmetic restoration; (2) passive prostheses; and (3) driven (active) prostheses. Cosmetic restoration describes a realistic silicone restoration meant to resemble the original anatomy, which almost exclusively provide psychosocial support for the individual, with very little functional capability. While invaluable in the rehabilitation process, cosmetic restorations are often abandoned within a few years.

Passive prostheses are devices which are not actively driven. These prostheses can be task-specific end-effectors, such as a grip shaped to fit onto a bicycle handlebar, which are donned and doffed for particular activities. The passive prostheses also include fixed posts that restore opposition grasp in the hand, either between a fixed-post thumb and intact fingers, or an intact thumb and fixed fingers. In recent years, this passive category has expanded to include adjustable opposition systems. These devices typically replace digits, and have one, two, or three joints mimicking the MCP, PIP, and DIP joints. The devices can also be applied to a socket on any upper limb amputation, such as an end effector for a mechanism (e.g., applied to a transradial amputation). They are spring loaded and adjustable to several postures representing different angles of digit orientation. Due to their robust nature and simplicity, passive prostheses are often the most utilized choice for return to work in manual labor environments.

Active prostheses can be powered by the body or by electricity. Body-powered devices are typically operated by a more proximal intact joint via linkages, cables, or straps. Some systems use cables run across the wrist joint to actuate artificial fingers in response to wrist flexion. One exemplary partial hand system uses a shoulder harness to drive fingers or a thumb in an open/close fashion. Electric partial hand solutions usually have individually motorized fingers and rely on a battery pack mounted on the forearm and myoelectric signals to generate several hand grasps with the fingers. One drawback of these systems is inhibition of wrist motion and sensitivity to moisture. Both body-powered and electrically driven partial hand systems have historically been restricted in their use environments due to weak forces and sensitive componentry.

BRIEF DESCRIPTION OF THE DRAWINGS

Many aspects of the present technology can be better understood with reference to the following drawings. The components in the drawings are not necessarily drawn to scale. Instead, emphasis is placed on illustrating clearly the principles of the present technology. Furthermore, components can be shown as transparent in certain views for clarity of illustration only and not to indicate that the component is necessarily transparent. Components may also be shown schematically.

DETAILED DESCRIPTION

A. Overview

Figure 1A:
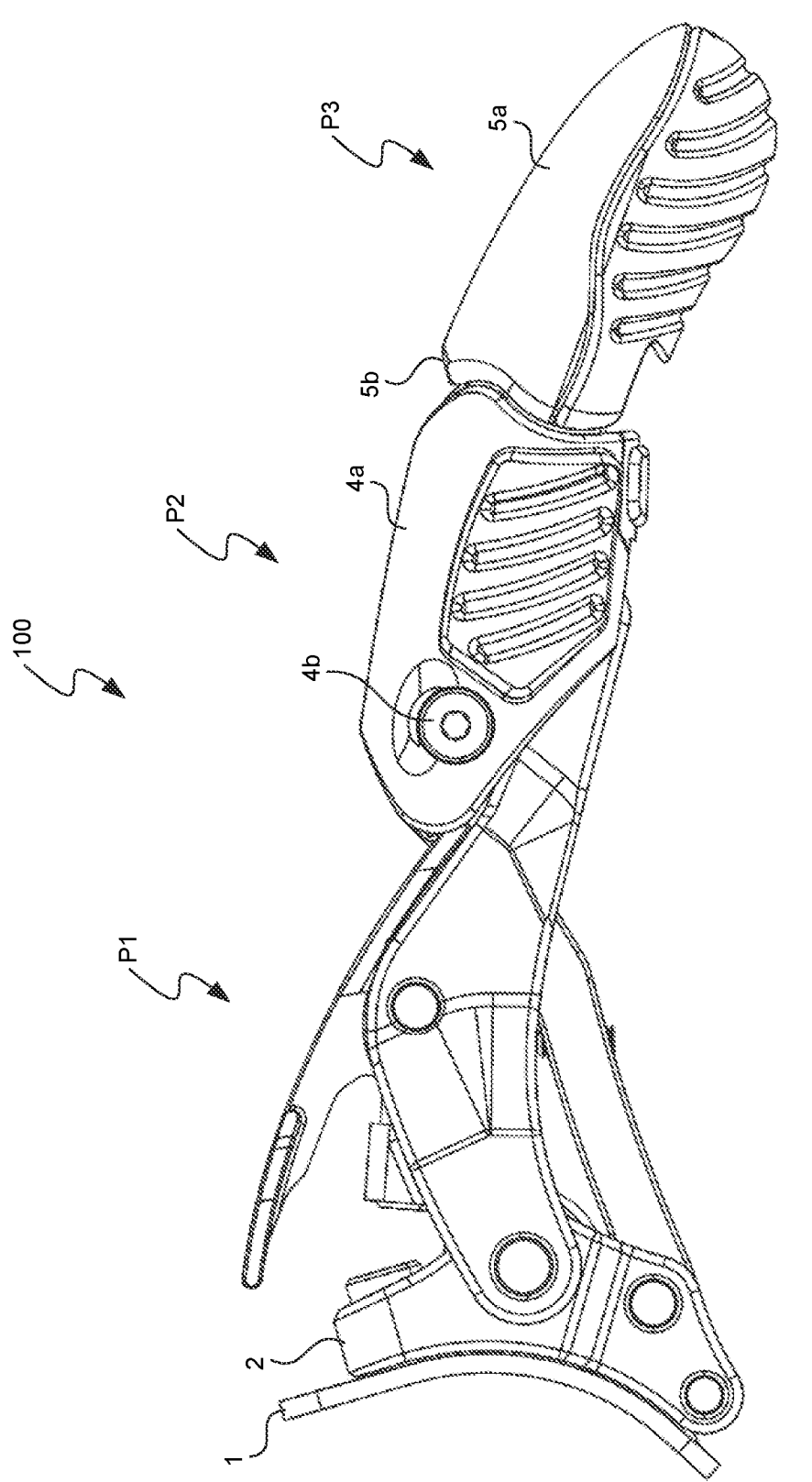
FIGS. 1A and 1B show elevation and perspective views, respectively, of a three-segment prosthetic digit configured in accordance with an embodiment of the present technology.

The present technology is directed to a prosthesis digit configured to replace a finger or thumb. Among other uses, the prosthesis is generally designed to provide adjustability, strength, and rigid opposition to a driven thumb or finger (intact or prosthetic). As explained in greater detail below, the prosthesis can be adjusted to multiple positions, representing increasing flexion of the digit, and is controlled by the interaction between a spring-loaded pawl and a rack with multiple teeth. In the illustrated embodiments, the prosthesis is shown having a rack located in a first segment and having ten positions corresponding to teeth of the rack; however, the rack can be located in other segments of the prosthesis (e.g., the second segment, the third segment, etc.) and can have any number of adjustment positions. When the digit is moved in flexion, the pawl moves freely over the rack teeth in the flexion direction, but is halted in the extension direction by the engagement of the pawl nose with the rack teeth. This ratcheting lock configuration accordingly provides the opposition required to hold objects in a flexion position, against opposable digits, and/or in the palm of the user's hand.

It is often desirable for prosthetic digits to be lightweight, compact, strong, and include natural movement patterns. Digits configured in accordance with the present technology can restore prehension in a person with missing finger(s) or thumb by providing opposition to the intact digits such that object manipulation and stabilization may be performed. The digit can exhibit a kinematic movement profile that is conducive to natural grasp patterns and provide opposition to forces in the extension direction via a spring-loaded pawl and locking rack ratchet mechanism, thereby allowing an individual to manipulate or stabilize objects. The digit may be spring-loaded in the extension direction by a torsion spring or other biasing member. The pawl may be automatically disengaged from the rack when the digit reaches full flexion, and the full flexion disengage stop may be adjustable. The pawl may be automatically engaged with the rack when the digit reaches full extension, and the extension stop may be adjustable. The pawl may contain a lateral feature that creates interference with the anchoring linkage under load and limits deflection of the structure. Practical consideration must also be given to the clinical socketing process, which determines the application of the digit to the user's hand via an intimately fitting mounting socket.

The digit can be moved to a new position by the user's opposing hand, other object, or by a routed tendon controlled by a more proximal joint or an external power source, among other movement options. The pawl mechanism and surrounding linkages can incorporate a toggle configured to selectively disable the ratcheting function and put the digit into a "free motion" mode, such that the ratchet mechanism does not halt extension of the digit. In this regard, the digit can function as an adjustable opposition system or a driven digit to provide grasp patterns such as the power hook, key, and cylindrical grasp, and other patterns and positions. The ability to perform these and other possible grasps is a portion of activities of daily living (ADL).

The terminology used in the description presented below is intended to be interpreted in its broadest reasonable manner, even though it is being used in conjunction with a detailed description of certain specific embodiments of the present technology. Certain terms may even be emphasized below; however, any terminology intended to be interpreted in any restricted manner will be overtly and specifically defined as such in this Detailed Description section. Additionally, the present technology can include other embodiments that are within the scope of the claims, but are not described in detail with respect to FIGS. 1-4B.

Reference throughout this specification to "one embodiment" or "an embodiment" means that a particular feature, structure or characteristic described in connection with the embodiment is included in at least one embodiment of the present technology. Thus, the appearances of the phrases "in one embodiment" or "in an embodiment" in various places throughout this specification are not necessarily all referring to the same embodiment. Furthermore, the particular features or characteristics may be combined in any suitable manner in one or more embodiments.

B. Selected Embodiments of Prosthetic Digits

Figure 1B:
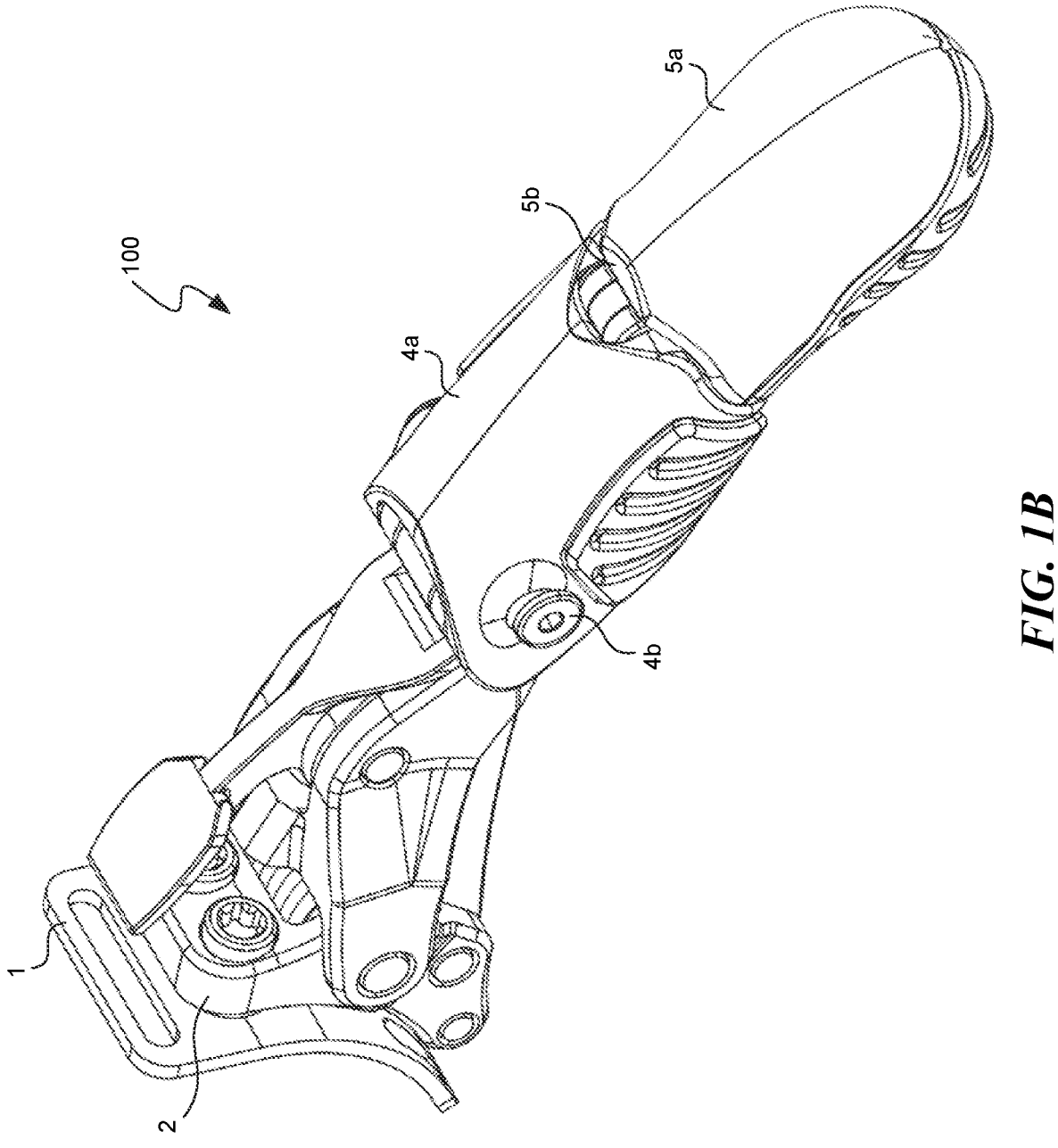

FIGS. 1A and 1B show elevation and perspective views, respectively, of a three-segment prosthetic digit 100 ("digit 100") configured in accordance with an embodiment of the present technology. The digit 100 may be mounted to a rigid or flexible substrate for use by the user (not shown), which can include a socket (e.g., a partial hand socket, transradial socket, etc.) or frame. The substrate secures the digit 100 to the user's hand in the approximate position of the user's anatomic digits. In some embodiments, it is possible to mount the digit 100 in a fashion that is non-anatomic, such as in the case of unique clinical presentations. The digit 100 generally includes an anchor piece 1 configured to be affixed to or embedded in the user's socket, and a base piece 2 of the digit 100 attached via fasteners or any other suitable attachment method. The digit 100 can be detached from the hand by removing the base piece 2 from the anchor piece 1. The digit 100 includes first, second, and third segments P1, P2, and P3, generally representing the bones of the finger, and the connections therebetween representing MCP, PIP, and DIP joints.

In the embodiment illustrated in FIGS. 1A and 1B, the digit 100 includes installed cosmetic and grip fairings 4a and 5a. The fairings 4a and 5a may include sections having increased grip materials configured to increase the friction of the fairings 4a and 5a. The fairing 4a may be mounted to the digit 100 by a fastener at a first mounting point 4b and the fairing 5a may be mounted to the digit 100 by a fastener at a second mounting point 5c (see FIG. 2B, fasteners not shown). One or more of the fairings 4a and 5a may include a relief cut 5b to allow an extended range of articulation of the P2 and P3 portions of the digit 100. These fairings may provide a silicone interface with objects for improved grip and allow the user to select designs and colors, or to replace these cosmetic pieces when wear occurs.

The anchor piece 1 may be configured to be attached to or embedded in the user's stump interface (not shown), and may include features designed to allow for successful integration with a fabricated socket. The materials can be temperature resistant to withstand the exothermic epoxy reactions expected in socket fabrication. The anchor piece 1 may also include various slots, holes, and other attachment features intended to allow for successful integration with carbon fiber, epoxy, silicone, and other anchoring methods typically used in the prosthetics field.

Figure 2A:
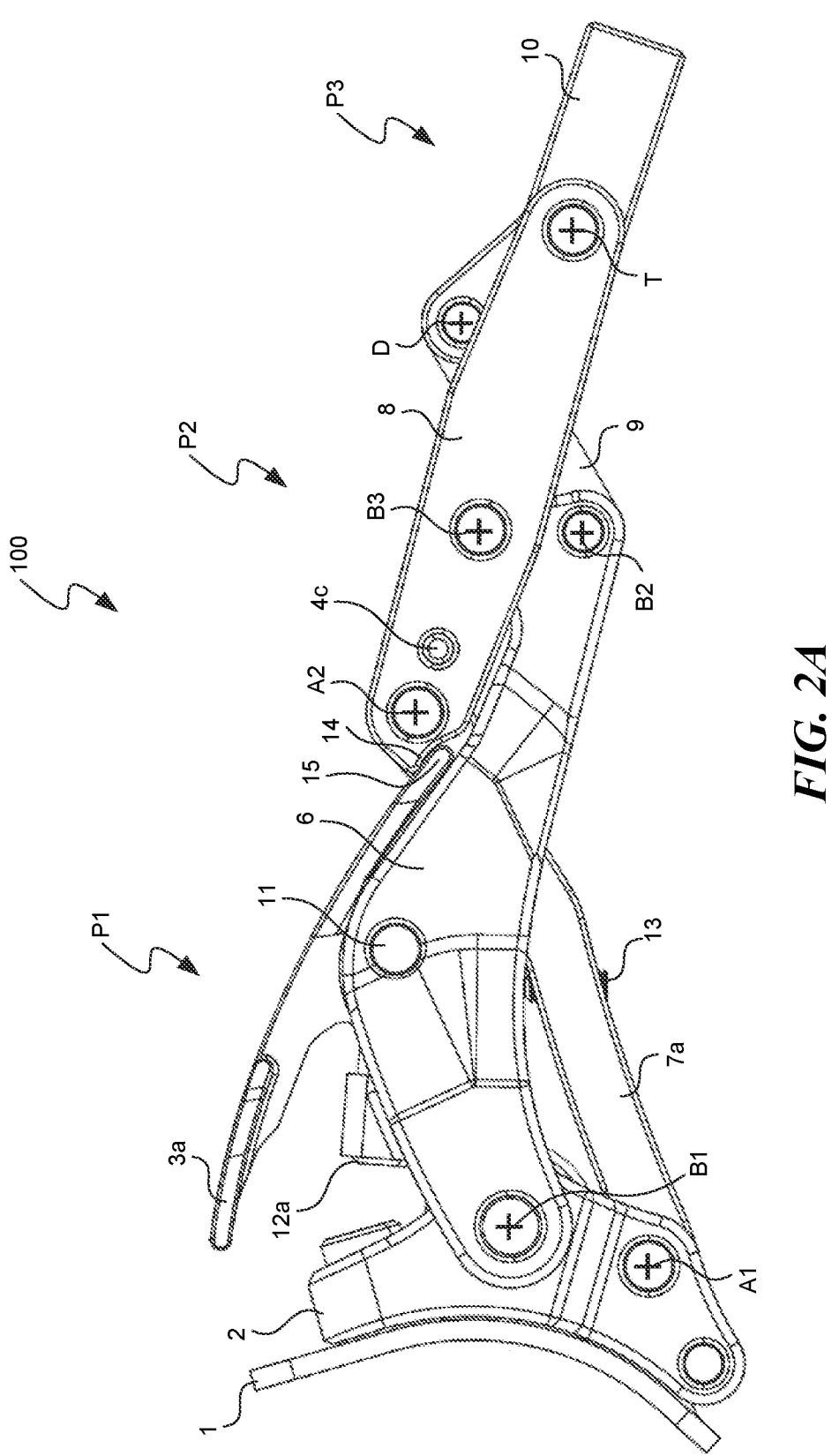
FIGS. 2A-2C show elevation, cross-section, and perspective views, respectively, of the three-segment prosthetic digit of FIGS. 1A and 1B, shown at full extension.
Figure 2B:
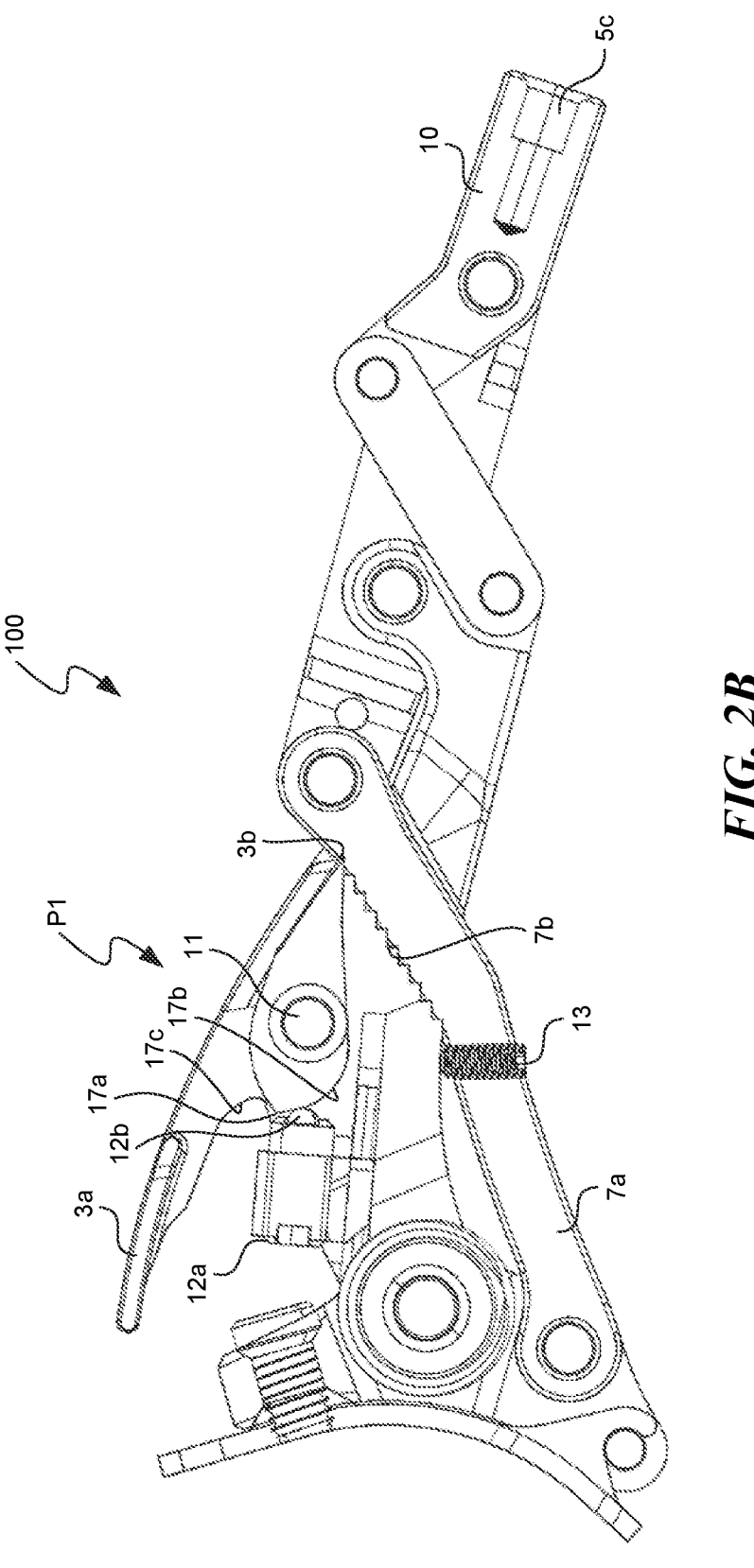
Figure 2C:
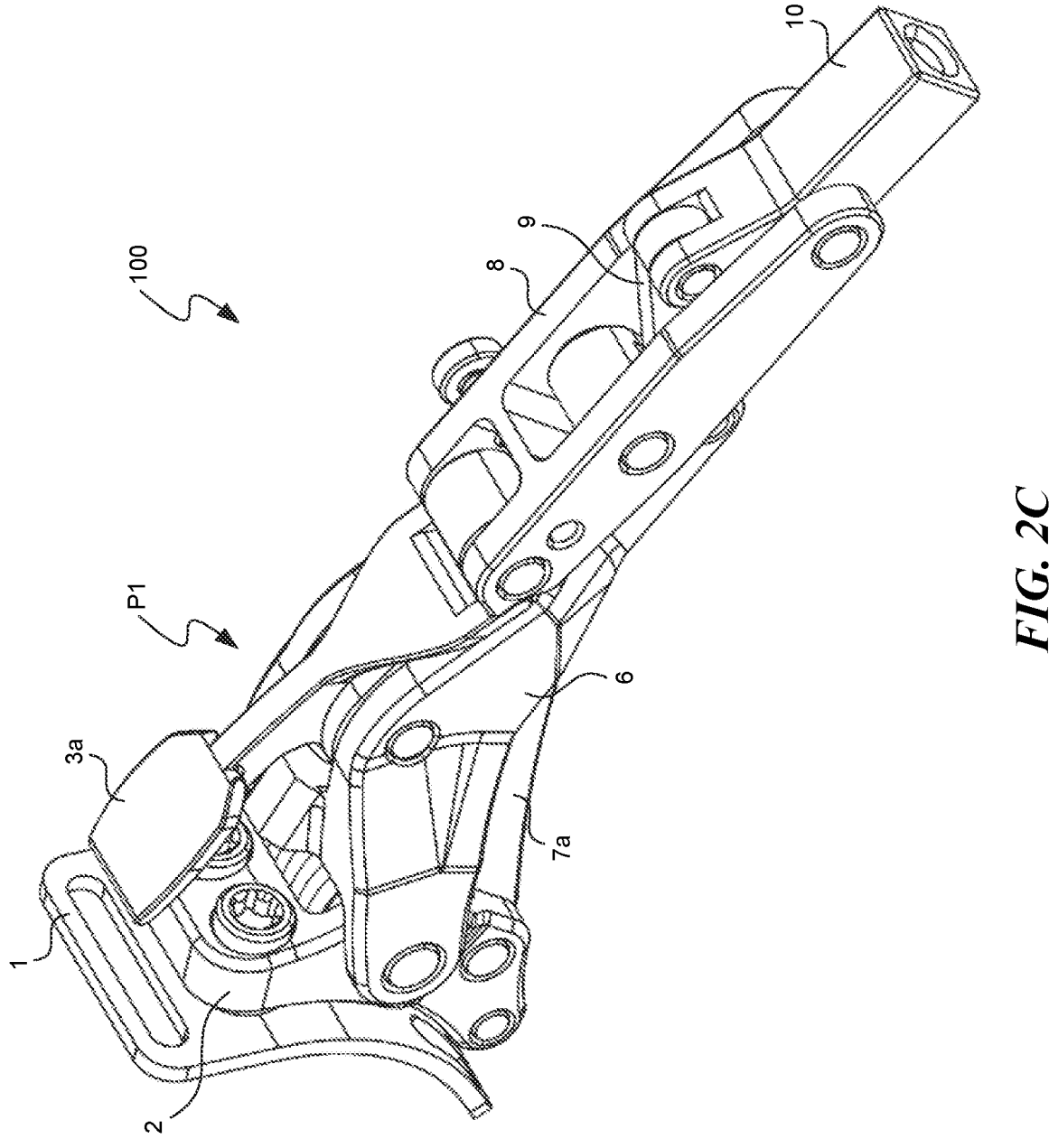

FIGS. 2A-2C show elevation, cross-section, and perspective views, respectively, of the prosthetic digit 100 of FIGS. 1A and 1B, still at full extension, but with fairings 4a and 5a removed for sake of illustration. The digit 100 may include a first pair of crossed linkages 6 and 7a via offset rotational joints A1, B1. The linkage 7a, for example, may comprise a plurality of rack teeth 7b designed to engage a pawl nose 3b of pawl 3a such that free motion is allowed in a flexion direction (e.g., movement toward the position shown in FIGS. 3A-3C), and a structural position lock is created in the extension direction. The rack teeth 7b are configured to interface with the pawl nose 3a and may be fabricated of hardened steel or other sufficiently strong and wear-resistant material(s). The pawl 3a is connected in a rotationally pinned manner with a pin 11 to the linkage 6, and may be engaged/disengaged with the rack teeth 7b via a spring-loaded detent 12a having a detent member 12b (see FIG. 2B) installed on a proximal underside of the pawl 3a and in the linkage 6. In other embodiments, rack teeth are located on or coupled to any suitable linkage of the digit 100 (e.g., linkages 6, 8, 9, 10, etc.), and in these configurations, a pawl can be configured to interface with the rack teeth allow free motion in the flexion direction and positionally lock the digit 100 in the extension direction.

The pawl 3a can be movable between at least two positions via the proximal spring-loaded detent 12a and 12b: (a) engaged, such that detent member 12b interfaces with an engaged surface 17b of the pawl 3a; and (b) disengaged, such that detent member 12b interfaces with a disengaged surface 17c of the pawl 3a. The engaged and disengaged surfaces 17b and 17c are separated by a transition peak 17a positioned to prevent the detent member 12b from settling between the engaged and disengaged surfaces 17b and 17c. In some embodiments, one or both of the engaged and disengaged surfaces 17b and 17c have a profile shape of an Euler curve (e.g., as viewed in the orientation of the digit 100 in FIG. 2B) configured to minimize force variance of the detent member 12b on the pawl 3a as the pawl 3a rotates through a range of motion. In these configurations, the pressure variance is minimized by maintaining a substantially constant contact angle between the detent member 12b and the engaged surface 17b and/or disengaged surface 17c.

To move the digit 100 in an extension direction, the pawl 3a is disengaged by moving the spring detent 12a to the disengaged position, where the detent member 12b interfaces with the disengaged surface 17c, thereby allowing the digit 100 to move freely toward extension by disengaging the pawl nose 3b from the rack teeth 7b. In the disengaged position, at full extension of the digit 100, the pawl 3a is forced back into the engaged position via a hard stop 14 (as best seen in FIG. 2A).

The spring-loaded detent 12a may be threaded and adjustable to account for tolerance stack ups. In the illustrated embodiments, for example, the spring-loaded detent 12a comprises a spring-loaded round plunger that deflects when pressed. The plunger surface slides over the proximal curved portion (e.g., 17b) of the pawl 3a and acts as a detent, holding the pawl 3a in the engaged or the disengage positions. Upon assembly, the spring detent linear position may be adjusted to an appropriate spring load corresponding to comfortable toggling between engaged and disengaged positions, and can be further adjusted to account for user preference, to correspond to particular installations, etc.

In some embodiments, the anchor piece 1 and base piece 2 may be configured such that only one attachment orientation between the components is possible. In other embodiments, however, the components have various possible attachment orientations. The base piece 2 may include a torsional spring 16 (see FIG. 3A) which exerts a constant extension-direction force on the system, acting to maintain the pawl nose 3b in an interface position with the rack teeth 7b and to return the system to extension when the pawl 3a is disengaged from the rack teeth 7b. The torsional spring 16, for example, may bias the digit 100 toward the extended position shown in FIGS. 1A-2C. The torsional spring 16 serves at least two purposes: (1) to force the pawl nose 3b into engagement with the rack teeth 7b such that a posture is held after being selected by the user; and (2) to automatically return the digit 100 to extension when the pawl nose 3b is disengaged from the rack teeth 7b.

Figure 2D:
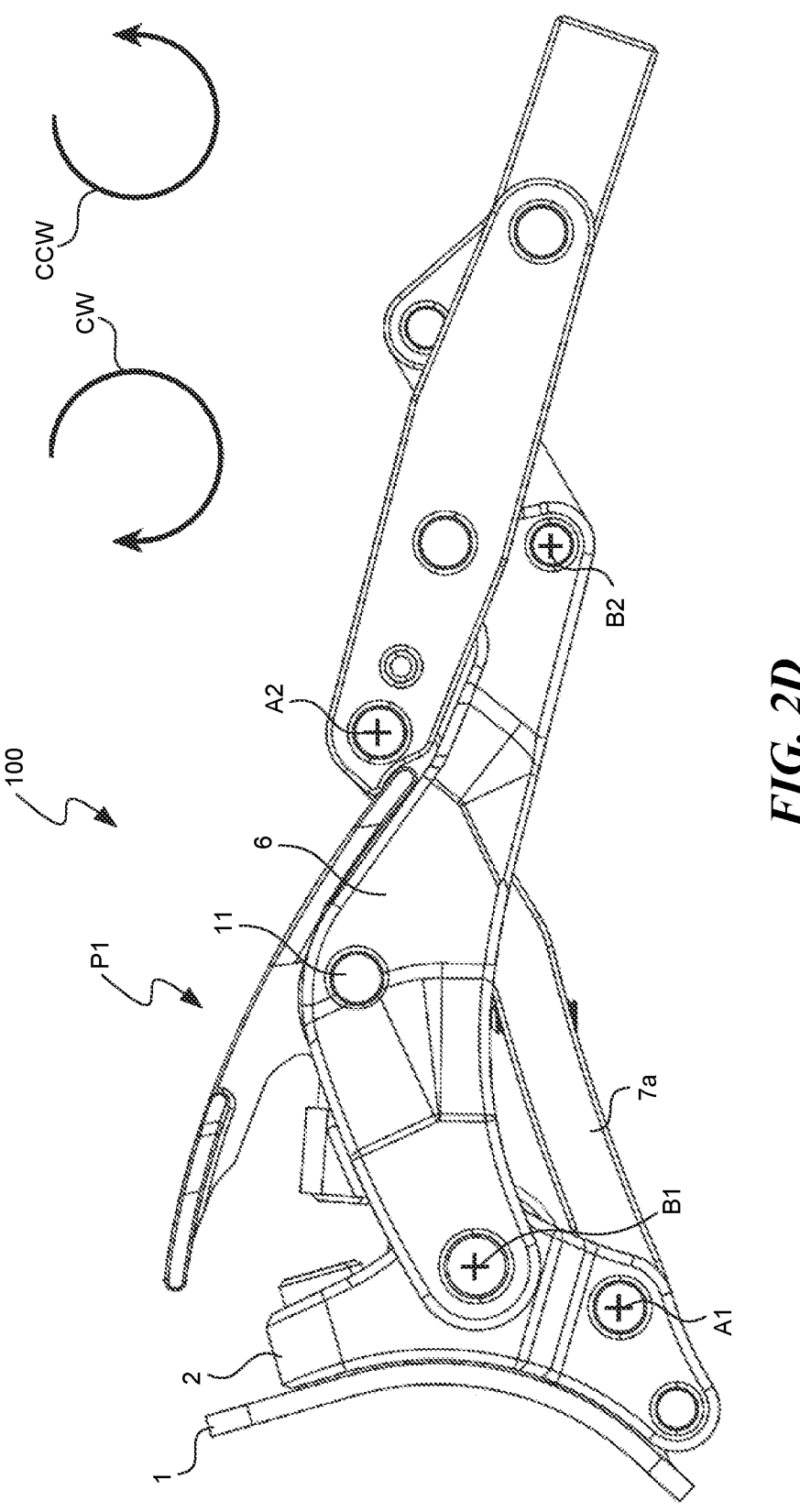
FIGS. 2D and 2E show elevation views of rotational connections of proximal and distal four-bar linkages, respectively, of the three-segment prosthetic digit of FIGS. 1A and 1B.
Figure 2E:
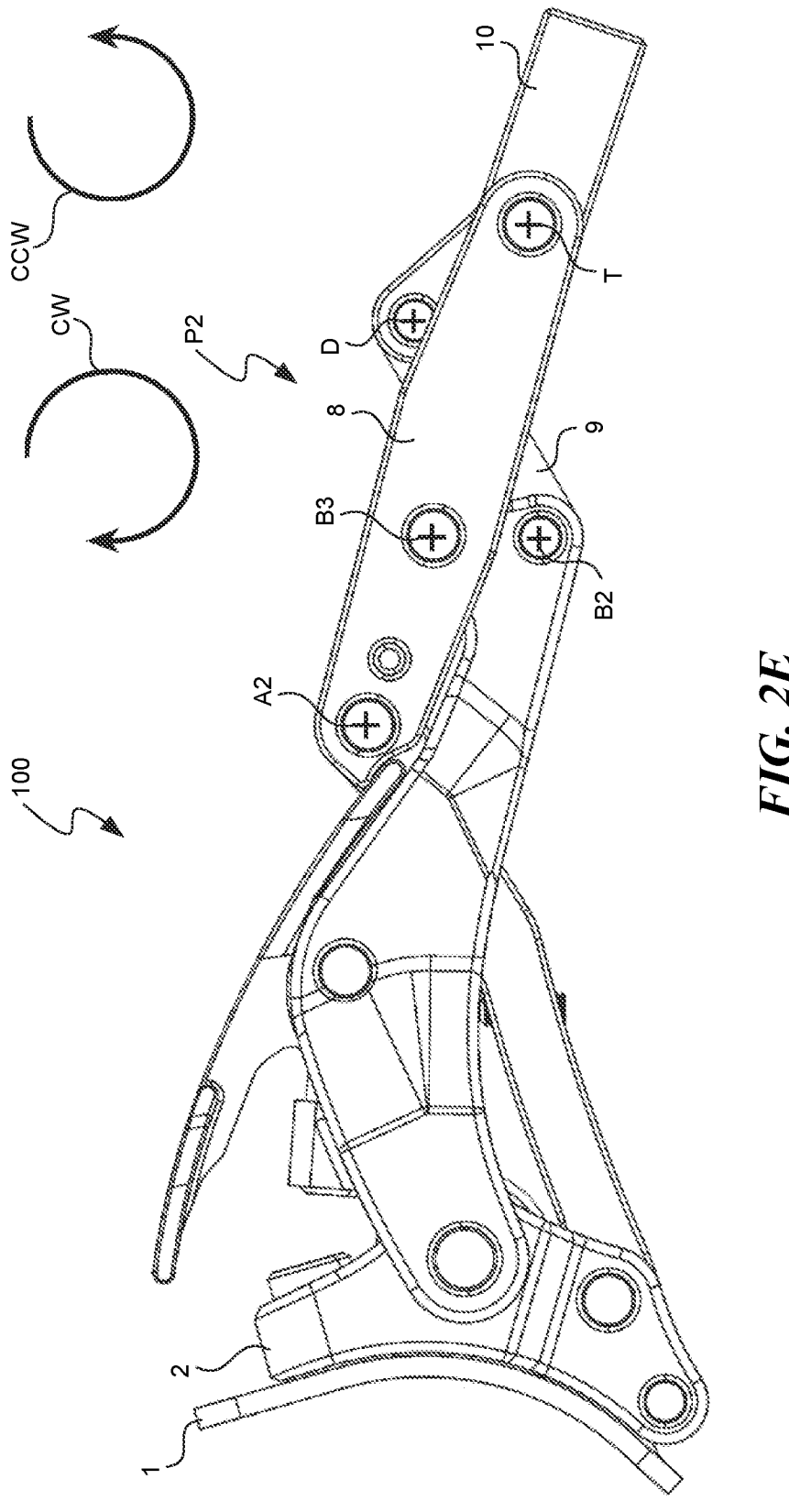

Referring to FIG. 2A, the digit 100 may further include linkages 8, 9, and 10, which form a portion of the coupled distal four-bar linkage (FIG. 2E) to interact with the proximal four-bar linkage (FIG. 2D) to create a relatively smooth, pleasing motion and kinematic space for the digit 100 similar to an anatomic finger. The linkages 6, 7a, 8, 9 and 10, via rotational connections, form two four-bar linkages in series. FIGS. 2D and 2E show elevation views of rotational connections of proximal and distal four-bar linkages, respectively, of the digit 100. FIG. 2D, for example, shows the rotational connections of the proximal four-bar linkage of the segment P1. The proximal four-bar linkage of the segment P1 is rotatably coupled to the base piece 2 at a rotational connection A1 and a rotational connection B1. As the digit 100 transitions from full extension (FIGS. 2A-2C) to full flexion (FIGS. 3A-3C), the linkages 6 and 7a rotate clockwise (direction CW in FIGS. 2D and 2E; counterclockwise direction CCW) about the rotational connections A1 and B 1. During such clockwise rotation, the linkages 6 and 7a rotate oppositely relative to each other about the pin 11. The relative rotation of the linkages 6 and 7a about the pin 11 causes a rotational connection B2 to move in a clockwise orbital path relative to a rotational connection A2 and spread apart from each other.

FIG. 2E shows rotational connections of the distal four-bar linkage of the segment P2. The distal four-bar linkage of the segment P2 is rotatably coupled to the proximal four-bar linkage of the segment P1 at rotational connections A2 and B2. During the rotation from full extension toward full flexion described above, the rotational connection B2 orbits clockwise around and spreads apart from the rotational connection A2 and causes the linkage 8 to rotate in a clockwise direction about a rotational connection B3 relative to at least the linkages 6 and 7a. Such rotation causes clockwise rotation of the linkage 9 about the rotational connection B2 with respect to the linkage 6. As the linkage 8 rotates clockwise, the linkage 10 also rotates clockwise with respect to the rotational connection B3, and further, the relative movement of the linkages 9 and 10 cause an opposite rotation of the linkages 9 and 10 about a rotational connection D, which in turn results in a clockwise rotation of the linkage 10 about a rotational connection T. The rotational positions of the linkages of the segments P1 and P2 described above can be further understood by comparing the position of the components in FIG. 2B with the position of the components in FIG. 3C.

The prosthetic digit 100 (hereinafter the "digit 100") opposes extension movement, allowing objects to be gripped and manipulated to hold objects in a flexion position, against the digit 100, and/or in the palm of the hand. A powerful orientation for the prosthesis is the "power hook grasp."

The aforementioned power hook grasp loading configuration can also cause a spreading deformation between the linkages 6 and 7a and force the nose of the pawl 3b in a proximal direction away from the rack teeth 7b. At certain deformation levels, the pawl 3a may over-toggle and flip, such that the nose 3b moves proximally and loses purchase on the rack teeth 7b, resulting in failure of the mechanism, and potential damage to components.

Figure 3A:
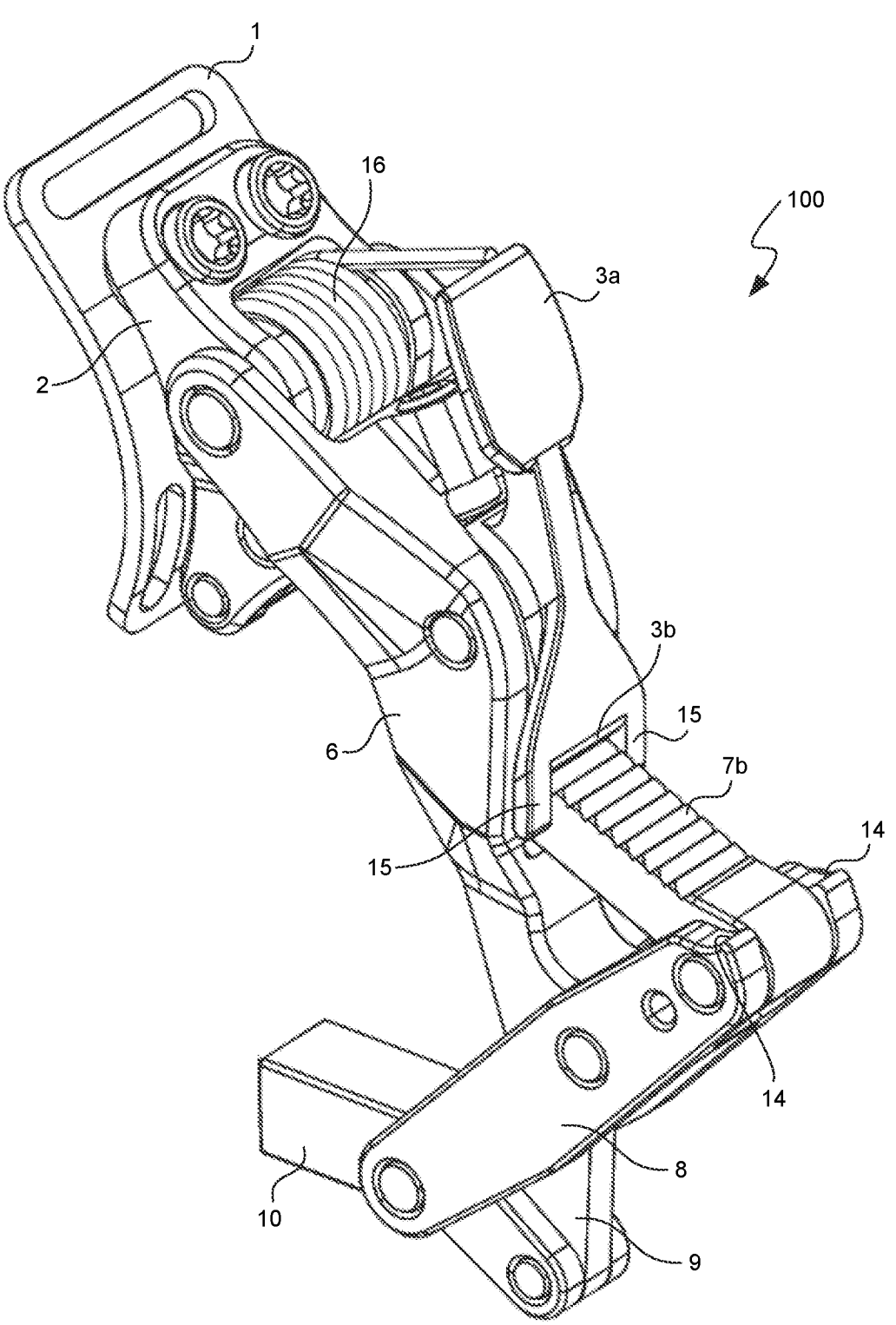
FIGS. 3A-3C show perspective, elevation, and cross-section views, respectively, of the prosthetic digit of FIGS. 1A and 1B, shown a full flexion.
Figure 3B:
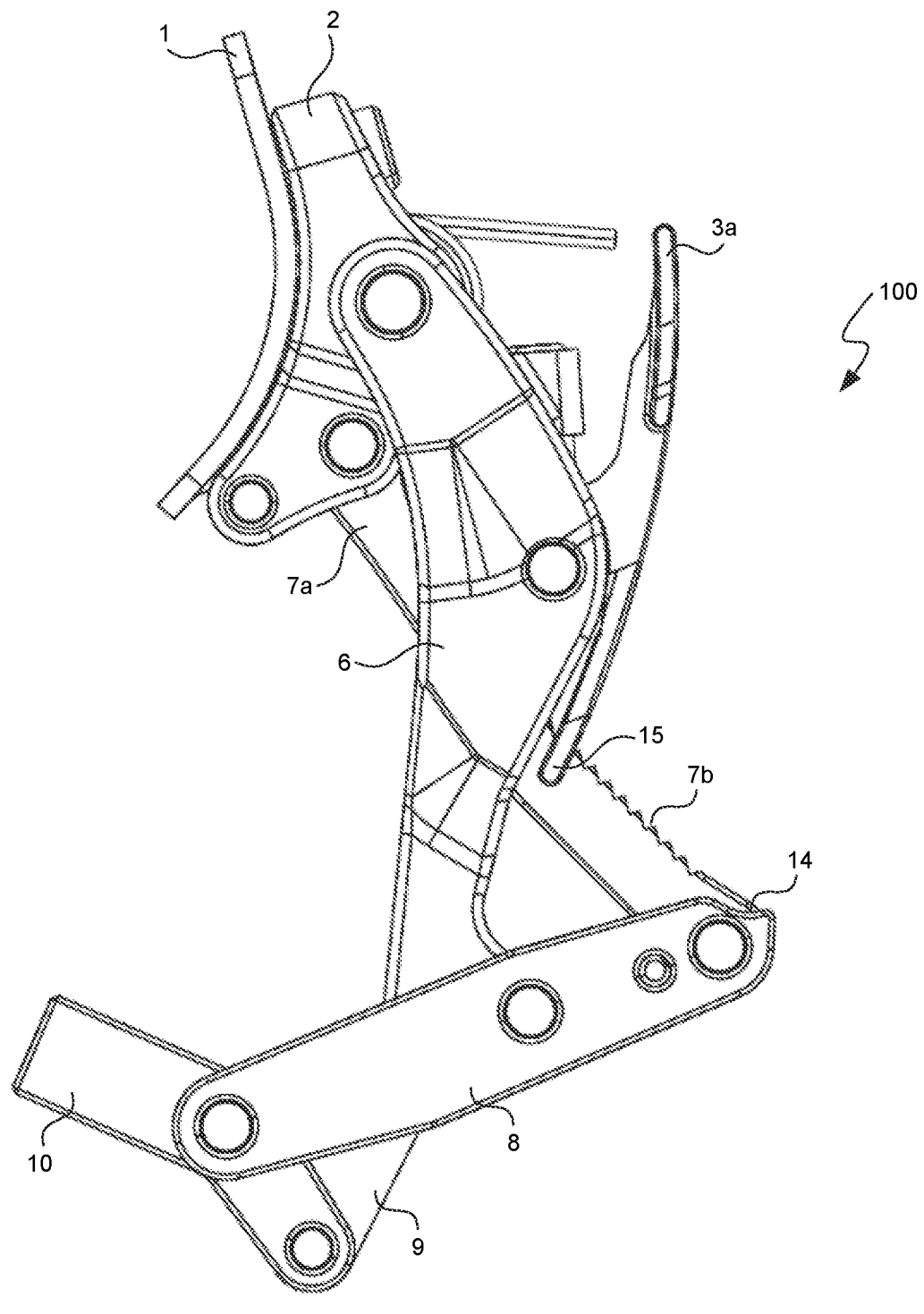
Figure 3C:
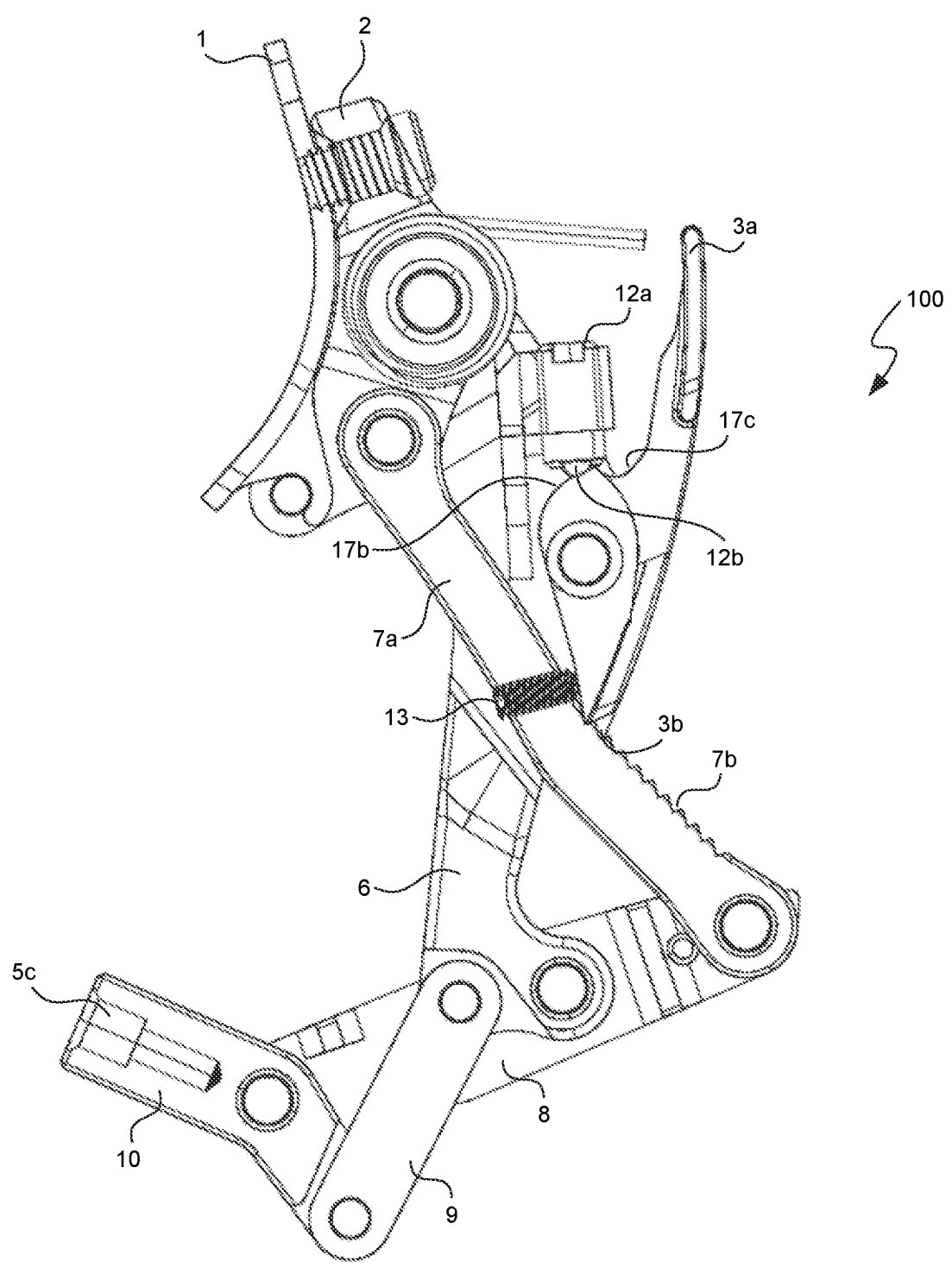

FIGS. 3A-3C show perspective, elevation, and cross-section views, respectively, of the prosthetic digit 100 of FIGS. 1A and 1B at full flexion, with fairings 4 and 5 removed for sake of illustration. At the position of full flexion, an adjustable hard stop 13 forces the pawl 3a into the disengage position, where the detent member 12b interfaces with the disengage surface 17c. The hard stop 13 allows a user to fully flex the digit 100 via a tabletop, opposing hand, or other object, and return it to an extension position (shown in FIGS. 1A-2C) via the torsional spring 16. The full flexion hard stop 13 may be adjustable, thereby allowing for variation in socket fabrication and finger placement. For example, if a clinical technician over-rotates the digit 100 toward the palm of the user's hand when embedding the anchor piece 1 in the socket, the digit 100 may be unable to achieve a non-adjustable full flexion hard stop disengage point due to the tip of the mechanism impacting the user's palm prematurely. The adjustability of the full flexion hard stop 13 allows for the functionality to be available, even in the case of poor positioning by a clinical technician. In one embodiment, the full flexion hard stop 13 is a set screw embedded into the rack linkage 7*a*. The position of the set screw 13 within the rack linkage 7*a* can be adjusted to change the pawl 3*a* disengage point. Other embodiments are possible for the adjustable full flexion hard stop 13 and are also within the scope of the present disclosure.

Similar adjustability may be provided for the extension pawl engage feature 14. In this regard, if a technician inadvertently over-rotates the position of the anchor toward the dorsum of the hand, the digit 100 would have a hyperextended neutral position, which is an impediment to function of the prosthesis device. The extension pawl engage feature 14 can be adjusted such that pawl 3*a* engagement is forced sooner than full extension to prevent the digit 100 from returning to a functionally impaired, hyperextended neutral position. As noted above, in other embodiments, the rack teeth are located on a different linkage of the digit 100, such as the linkage 8, 9, 10, etc., and the pawl, hard stop, and extension pawl engage feature can be positioned to interface with the rack teeth on a different linkage.

Embodiments of the present technology are expected to provide a number of advantages over conventional devices including, among other advantages: (1) lower weight; (2) integration of the rack and pawl into a proximal four-bar configuration where forces are relatively low; (3) the full flexion pawl disengage is adjustable, allowing for adjustments when poor placement occurs during mounting socket fabrication; (4) the extension pawl engage is adjustable, allowing for adjustments when poor placement occurs during mounting socket fabrication; (5) the pawl dog feature is engaged during high loads and deflection, acting to lessen deflection and increase the load bearing capability of the device; and (6) attachment points for consumable cosmetic covers including aesthetic features and functional gripping features for improved object manipulation. The embodiments are also suitable for dynamic tendon-driven digits. As compared with conventional prosthesis digit technology, the present technology is further expected to provide enhanced application robustness, cosmetic appeal, and serviceability.

Figure 4A:
FIGS. 4A and 4B show elevation views of two-segment prosthetic digit configured in accordance with another embodiment of the present technology.
Figure 4B:
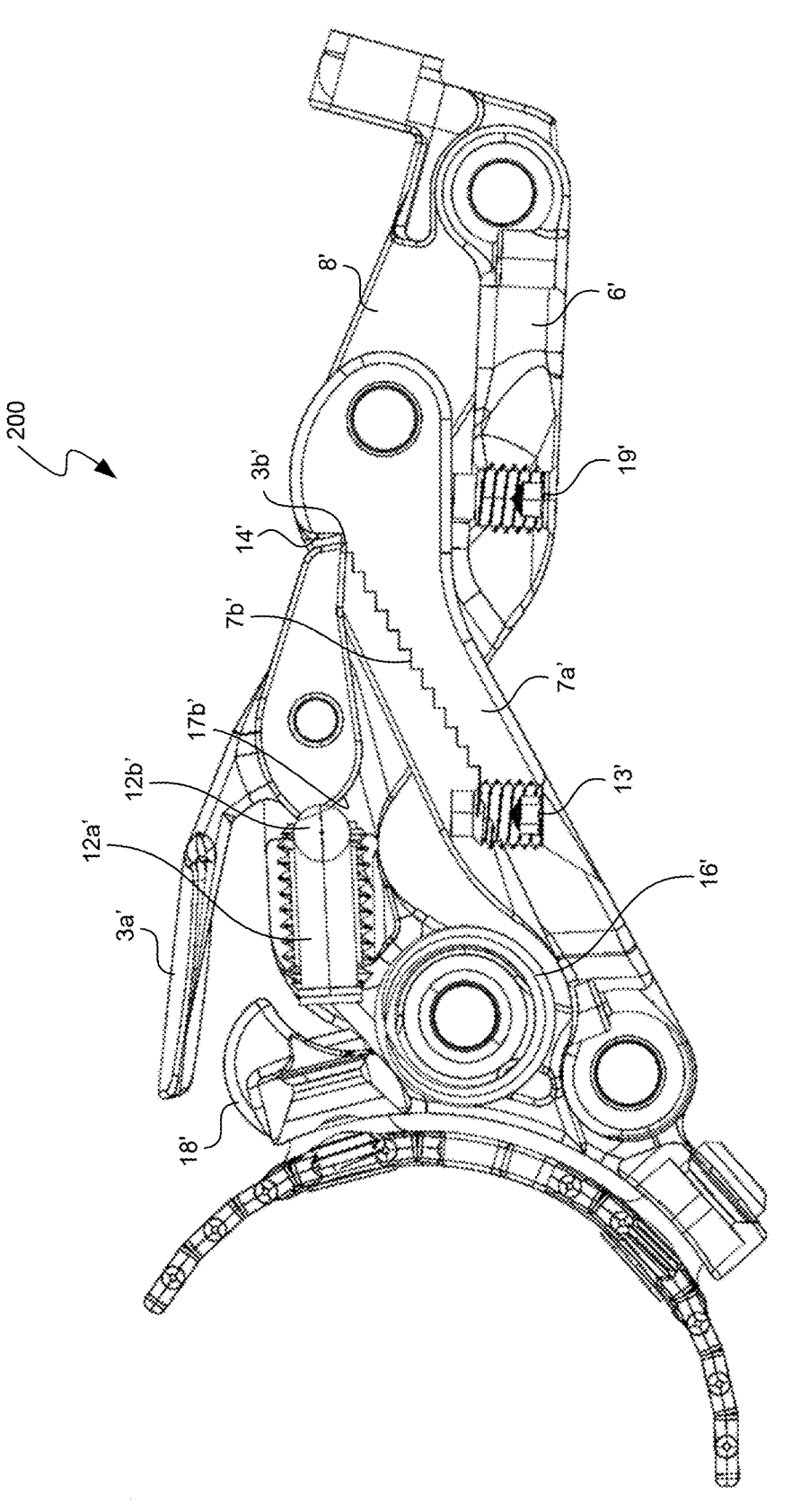

FIGS. 4A and 4B show elevation views of a two-segment prosthetic digit 200 ("digit 200") having a similar configuration of the proximal four-bar linkage of the digit 100, including an anchor 1' and linkages 2', 6', 7', and 8', but eliminating the linkages 9 and 10 of the digit 100. The digit 200 provides a fixed distal joint and only one four-bar linkage, and may include fairings 20' and 21' configured to function similarly to fairings 4*a* and 5*a* of the digit 100. Some components of the digit 200 are similar to those of the digit 100, but are denoted with a prime (e.g., 2', 3', etc.) for the digit 200. Like reference numerals of the digit 200 in FIGS. 4A and 4B to those of the digit 100 in FIGS. 1-3C, should not necessarily be construed as the exact same component, and the components in FIGS. 4A and 4B may differ in shape, size, function, etc. to those in FIGS. 1-3C.

Referring to FIG. 4B, the extension pawl 3*a*' engage feature is a mechanical stop 18' on the base piece 2' that impacts the pawl 3*a*' on the bottom of its paddle at extension and forces the detent member 12*b*' into engagement with the surface 17*b*'. In another embodiment, as described above, the extension pawl engage feature is a mechanical stop 14' positioned at the distal end of the pawl 3*a*' and configured to engage the dorsal surface of the pawl nose 3*b*' to force the detent member 12*b*' into engagement with the surface 17*b*'. In some embodiments, the extension hard stop 14' is adjustable, such as by using an adjustable stop 19'. In other embodiments, the extension pawl engage feature may have a different arrangement and/or include different features. Both the adjustable full flexion hard stop and the adjustable extension pawl engage features can reduce the usable range of teeth on the rack 7*b*' to customize the digit 100 to an individual user.

In some embodiments, the pawl 3*a*' may have a paddle portion on the dorsal side to allow a user to manually disengage the ratchet mechanism (the pawl nose 3*b*' and the rack teeth 7*b*'). The paddle portion can be placed in various locations and still allow for a manual disengagement of the ratchet lock. The bottom surface of the pawl 3*a*' is configured to engage with the adjustable full flexion hard stop 13' such that at full flexion the pawl 3*a*' will be forced into a disengaged position and will return the structure to full extension via the spring force generated by the torsional spring 16'. The dorsal surface of the nose of the pawl is designed with a feature that interfaces with the adjustable extension engage feature 14' to return the pawl 3*a*' to the engaged position at full extension.

The present technology may utilize two or three pairs of offset rotational joints, connected via rigid linkages, to generate coupled four-bar movement and to mimic the sliding condylar motion seen in natural anatomy, providing a compact and realistic motion space. In the embodiments of the digit 100 described above with reference to FIGS. 1A-3C, segments P1, P2, and P3 represent the bones of the finger and the connections therebetween represent the MCP, PIP, and DIP joints. In the embodiments of the digit 200 described above with reference to FIGS. 4A and 4B, segments P1 and P2 represent the bones of the finger and the connections therebetween represent only the MCP and PIP joints, with a fixed DIP joint. Other configurations are also within the scope of the present disclosure.

C. Conclusion

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. Moreover, the various embodiments described herein may also be combined to provide further embodiments. Reference herein to "one embodiment," "an embodiment," or similar formulations means that a particular feature, structure, operation, or characteristic described in connection with the embodiment can be included in at least one embodiment of the present technology. Thus, the appearances of such phrases or formulations herein are not necessarily all referring to the same embodiment.

For ease of reference, identical reference numbers are used to identify similar or analogous components or features throughout this disclosure, but the use of the same reference number does not imply that the features should be construed to be identical. Indeed, in many examples described herein, identically numbered features have a plurality of embodiments that are distinct in structure and/or function from each other. Furthermore, the same shading may be used to indicate materials in cross section that can be compositionally similar, but the use of the same shading does not imply that the materials should be construed to be identical unless specifically noted herein.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Where the context permits, singular or plural terms may also include the plural or singular term, respectively. Additionally, the term "comprising" is used throughout to mean including at least the recited feature(s) such that any greater number of the same feature and/or additional types of other features are not precluded. Directional terms, such as "upper," "lower," "front," "back," "vertical," and "horizontal," may be used herein to express and clarify the relationship between various elements. It should be understood that such terms do not denote absolute orientation. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A prosthetic digit, comprising:
a first linkage coupled to a base, wherein the first linkage comprises a plurality of rack teeth;
a second linkage coupled to the base in an overlapping arrangement with the first linkage, wherein the first linkage and second linkage are each configured to pivot with respect to the base during flexion and/or extension of the prosthetic digit; and
a pawl operably coupled to the second linkage, wherein the pawl is movable between—
a first engaged position in which a distal nose of the pawl abuts a first one of the plurality of rack teeth,
a second engaged position in which a distal nose of the pawl abuts a second one of the plurality of rack teeth different from the first one of the plurality of rack teeth, and
a disengaged position in which the distal nose is spaced away from and does not contact the rack teeth during flexion and/or extension of the prosthetic digit.

2. The prosthetic digit of claim 1, further comprising
a third linkage pivotably coupled to a distal end of the first linkage, wherein the third linkage comprise a stop surface, and wherein the pawl is configured to abut the stop surface to return the pawl to the first engaged position.

3. The prosthetic digit of claim 1, further comprising a pawl dog, and wherein, when the pawl is in the first engaged position, the pawl dog extends from the distal nose of the pawl to engage a side of the first linkage.

4. The prosthetic digit of claim 3 wherein the pawl dog is configured to contact the first linkage during loaded articulation of the prosthetic digit.

5. The prosthetic digit of claim 1, further comprising:
a third linkage pivotably coupled to the base and a proximal end of the first linkage; and
a fourth linkage pivotably coupled to the base and a proximal end of the second linkage.

6. The prosthetic digit of claim 5 wherein pivotable movement of the first elongate linkage in a first direction with respect to the base causes pivotable movement of the third elongate linkage in a second, opposite direction.

7. The prosthetic digit of claim 1 wherein the first linkage and second linkage are pivotably coupled to the base.

8. The prosthetic digit of claim 1, further comprising an anchor configured to be affixed to or embedded in a socket of a user's hand, and wherein the base is fixedly coupled to the anchor.

9. The prosthetic digit of claim 1, further comprising a biasing member positioned to rotationally urge a distal end of one of the first and second linkages toward a distal end of the other of the first and second linkages.

10. The prosthetic digit of claim 9 wherein the biasing member is positioned to urge the prosthetic digit toward an extended position, abutting the distal nose against the first one of the plurality of the rack teeth in the first engaged position of the pawl.

11. The prosthetic digit of claim 10, further comprising an adjustable flexion member carried by the first linkage, wherein the adjustable flexion member is positioned to rotate the pawl to the disengaged position when the prosthetic digit reaches a set maximum flexion position.

12. The prosthetic digit of claim 1, further comprising an adjustable extension member configured to abut a surface to limit the rotation of the prosthetic digit at a maximum extension position.

13. The prosthetic digit of claim 1, further comprising a detent member configured to contact one of (a) a concave disengaged surface on the pawl to retain the pawl in the disengaged position and (b) a convex engaged surface on the pawl to retain the pawl in the first engaged position.

14. The prosthetic digit of claim 1, further comprising a fairing coupled to and covering at least a portion of the first linkage and the second linkage.

* * * * *